United States Patent
Langen et al.

(10) Patent No.: US 8,162,862 B2
(45) Date of Patent: Apr. 24, 2012

(54) DRESSING MATERIAL

(75) Inventors: Guenter Langen, Wolfstein (DE); Marita Meister, Kaiserslautern (DE)

(73) Assignee: Karl Otto Braun GmbH & Co. KG., Wolfstein (DE)

( * ) Notice: Subject to any disclaimer, the term of this patent is extended or adjusted under 35 U.S.C. 154(b) by 593 days.

(21) Appl. No.: 11/941,775

(22) Filed: Nov. 16, 2007

(65) Prior Publication Data

US 2008/0086068 A1 Apr. 10, 2008

Related U.S. Application Data

(63) Continuation of application No. PCT/EP2006/004713, filed on May 18, 2006.

(30) Foreign Application Priority Data

Jun. 8, 2005 (DE) .......................... 10 2005 026 298

(51) Int. Cl.
 *A61F 5/00* (2006.01)
(52) U.S. Cl. ........................................... 602/1; 442/103
(58) Field of Classification Search .................. 604/1, 6, 604/7, 8, 9, 10, 11; 428/902, 903; 442/103, 442/164, 180, 313, 312, 306
 See application file for complete search history.

(56) References Cited

U.S. PATENT DOCUMENTS

| | | | |
|---|---|---|---|
| 6,358,220 B1 * | 3/2002 | Langen et al. | 602/8 |
| 6,946,168 B2 * | 9/2005 | Senga et al. | 428/1.1 |
| 2007/0255189 A1 * | 11/2007 | Halanski et al. | 602/8 |
| 2007/0259598 A1 * | 11/2007 | Ribi | 446/385 |

FOREIGN PATENT DOCUMENTS

| | | |
|---|---|---|
| DE | 35 44 151 A1 | 6/1987 |
| EP | 1 029 521 A2 | 8/2000 |
| JP | 62263112 | 11/1987 |
| JP | 2000296147 | 10/2000 |
| JP | 2001096146 | 4/2001 |
| JP | 2004532713 | 10/2004 |

OTHER PUBLICATIONS

PCT/EP2006/004713 International Search Report, Sep. 4, 2006.

\* cited by examiner

*Primary Examiner* — Arti Singh-Pandey
(74) *Attorney, Agent, or Firm* — Brinks Hofer Gilson & Lione

(57) ABSTRACT

The invention relates to a dressing material comprising a thermoplastic, the thermoplastic being applied to a first textile web and the thermoplastic containing a first microencapsulated dye. Furthermore, the invention comprises a production method and a bandage, an orthopedic support dressing and an application.

8 Claims, 1 Drawing Sheet

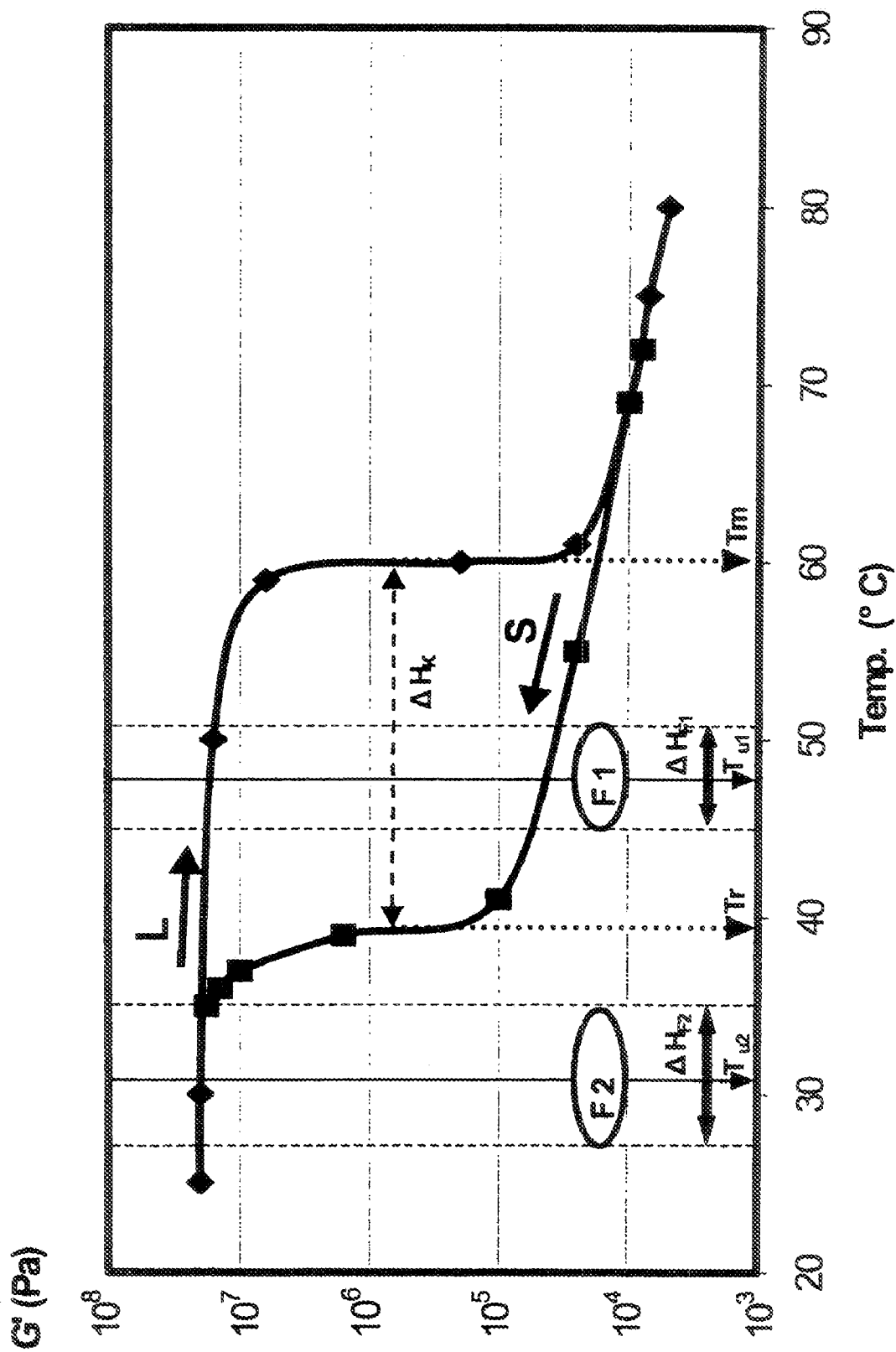

DRESSING MATERIAL

CROSS-REFERENCE TO RELATED APPLICATIONS

This application is a continuation of International Application No. PCT/EP2006/004713 filed on May 18, 2006, which claims the benefit of DE 10 2005 026 298.8, filed Jun. 8, 2005. The disclosures of the above applications are incorporated herein by reference.

FIELD

The disclosure relates to a dressing material and method for its production.

BACKGROUND

The statements in this section merely provide background information related to the present disclosure and may not constitute prior art.

To produce dressings intended to support and stabilize limbs, plaster cast materials have been known for quite some time. In addition, alternative dressing material based on polymers has been in use for a while. Compared to the plaster casts, this material has the advantage that it has improved mechanical properties, in particular, washability and water resistance. In addition, the polymer material can be applied and cured more quickly and has a lower weight, thus guaranteeing increased comfort when wearing it, and improved mobility. Finally, compared to cast materials, the dressing materials based on polymers have the advantage that they allow x-rays to penetrate more easily and therefore enable x-ray check-ups without having to remove the dressing.

Both the plaster cast materials and the dressing materials based on polymers substantially comprise an organic or inorganic textile carrier material and the cast or polymer material applied thereon. With respect to the polymer materials, a differentiation is made between irreversibly curable materials and thermoplastic, reversibly deformable materials.

As irreversible polymer dressing materials, primarily water-curable systems are known, which comprise reactive polyurethane prepolymers as the curable polymer component, wherein the prepolymers harden upon contact with water. As long as the polymer is not hardened, the individual layers of the dressing material can be glued to each other, ultimately obtaining a dressing comprising a plurality of material layers.

In the case of thermoplastic reversibly deformable dressing materials, the self-adhesive property is achieved by heating the thermoplastic to the respective melting/softening temperature or above, so that the layers then enter a permanent bond when they are applied. As the material cools, it solidifies again, however for some time it still remains plastically deformable, even at temperatures below the melting point. Polymers of this type follow a hysteresis curve with respect to their melting and solidification properties. After the thermoplastic has completely solidified, a stable, multi-layer, bonded dressing system is obtained.

A corresponding dressing material is known, for example, from EP 1 029 521 A2, which discloses a thermoplastic dressing material that is rigid or semi-rigid at temperatures of 50° C. and below and self-adhesive in the pliable state, comprising a first textile web and a thermoplastic polymer applied to the first textile web, the thermoplastic having a melting point ranging from 55° C. to 90° C., and at least one second textile web that is applied to this material dressing. This allows for the adhesion of the layers on the finished dressing not to be negatively influenced, while the bandage is easy to unroll, even after squeezing out the remaining water after heating in a water bath. Thus the protective layer does not have to be removed, which clearly increases the ease of handling. Finally, in this way, a second, outwardly directed textile surface is achieved, which helps improve the surface character of the finished dressing. So as to create a colored dressing, color pigments may be added.

The disadvantage of the above-described design is that the color pigments can come in direct contact with the wearer as well as with the technician when applying the cast, and may result in undesirable skin reactions, such as skin irritation, sensitization or allergic reactions, due to the toxic components or decomposition products of the dyes. As a result, such colored cast bandages are associated with the problem that they cannot be worn permanently directly on the skin without additional skin-protecting materials, such as gauze, tube bandages, and crepe.

SUMMARY

The disclosure provides a dressing material and a method for producing a corresponding dressing material, wherein the color variants of a corresponding cast bandage can be implemented without certain color pigments coming in direct contact with the skin of the technician and/or the patient, so that it is prevented at the same time that the wearer of a corresponding colored cast bandage can come in contact with toxic color components. Another variation of present disclosure implements colored cast bandages, which can be worn permanently for several weeks directly on the skin without the use of skin-protecting materials, such as gauze, tube bandages or crepe.

DRAWINGS

The drawings described herein are for illustration purposes only and are not intended to limit the scope of the present disclosure in any way.

In order that the invention may be well understood, there will now be described an embodiment thereof, given by way of example, reference being made to the accompanying drawing, in which:

FIG. 1 is a graph illustrating a temperature-dependent course of the storage modulus G' (elastic portion of the shear modulus)

DETAILED DESCRIPTION

The following description is merely exemplary in nature and is not intended to limit the present disclosure, application, or uses.

The present disclosure provides a dressing material according to claim 1, a method according to claim 7, a bandage, and an application and an orthopedic support dressing, wherein the thermoplastic polymer comprises a first microencapsulated dye. Since the dye is encompassed by the microcapsule casing, it is possible that the dyed bandage material does not result in any direct contact between the skin and the dyes and therefore skin irritations caused by toxic dye components, such as azo, amine or heavy metal components, are avoided.

The corresponding dye micro-capsules, which may in particular have a particle diameter of 0.5 to 20 μm, comprise a thin casing, which can be made, for example, of an aminoplast or a urea-formaldehyde resin etc. The dye can be directly encapsulated in the casing. It may also be provided that such micro-capsules, in addition to the color pigment and the casing, comprise a solvent or wax component. The dye micro-capsules may be added to the thermoplastic resin in a weight proportion ranging between 0.1 and 8% by weight, particularly 0.5 to 4% by weight, depending on the desired color depth.

According to one form, it is furthermore provided that micro-capsules with temperature-sensitive, or thermochromic, dyes are used, which assume, for example, an intensive hue such as red, blue, green etc. at room temperature and a colorless or transparent state at a certain color-turning temperature Tu. If such a thermochromic dye is used for a thermoplastic bandage, the color-turning temperature of the thermochromic dye may be adjusted within certain limits to the melting point/softening temperature of the thermoplastic resin. In this way, the problem experienced until now is solved, according to which the thermoplastic dressing materials failed to indicate their respective states, which is to say whether they were substantially in the application state—in which the dressing is thermally activated (temperature T higher than Tm=melting temperature of the polymer) and therefore deformable—or the functional state—in which the dressing in the cooled state at room temperature (temperature T lower than Tr=solidification temperature of the polymer) due to its regained rigidity develops the supporting effect as a rigid bandage—which would be particularly desirable when the user has to redo previously applied dressings, but also throughout the entire duration of wear of the dressing by the patient. As a result, it is possible that the supporting effect of the dressing decreases under the effects of sun shine or another heat application. An indication of the state would therefore be desirable.

Thermochromic dyes of this type, which are micro-encapsulated, are known, for example, from DE 35 44 151 C2, the contents of which are incorporated herein by reference in their entirety.

Furthermore, also U.S. Pat. No. 5,412,035, the contents of which are incorporated herein by reference in their entirety, discloses a dressing material comprising an adhesive, which acts as a pressure-sensitive hot-melt adhesive only at higher temperatures, however which has no adhesive properties at ambient temperatures. Furthermore, this publication reveals that additives are provided, which either indicate a change in color or a change from transparent to opaque when the adhesive is heated above a certain predefined temperature or cooled below it.

According to the disclosure, particularly the reversible color change is advantageous. According to the disclosure, it is also possible, by making a targeted selection of the wax or solvent component in the micro-encapsulated dyes, to adjust the color-turning temperature Tu of the thermochromic dye to any arbitrary temperature between 20° C. and 80° C. This is achieved in that solvent or wax components are selected which in turn have a melting or softening point that corresponds to the desired turning point of the thermochromic dye. In particular, it is possible to adjust the color-turning temperature Tu of the thermochromic dye to the melting point Tm or solidification point Tr of the thermoplastic resin. Likewise, it is possible to adjust the color change to the hysteresis range $\Delta H_K$, the functional state or the application state of the thermoplastic resin. For this purpose, wax or solvent components are selected which have a melting or solidification point that corresponds to the melting point Tm or solidification point Tr of the thermoplastic resin. However, it may also be provided that wax or solvent components are selected which have a melting or softening point that is within the temperature range of the application state or within the temperature range of the functional state. In one form, such reversible color changes are made, which upon heating achieve a change from an intensive hue particularly to a colorless or transparent color.

This color change signals to the user that the substance has been properly activated as a function of the temperature and duration of storage of the dressing material in a heater such as a water bath, heating cabinet or the like, for heating purposes. During the application of the dressing material, the cooling of the thermoplastic resin causes the original hue to return below the color-turning temperature Tu of the thermochromic dye, signaling to the user or patient that the dressing material is solidifying and hardening, thus achieving the desired support effect. The temperature-sensitive color change effect occurs reversibly—within a hysteresis range $\Delta H_F$ around the color-turning temperature Tu—and accompanies every activation and solidification cycle, for example also during subsequent partial shaping by means of hot air, hair dryer etc. The adjustment of the turning point is performed by means of the solvent or wax component of the dye micro-capsules and can be varied arbitrarily within a wide range of 20° C. and 80° C. as a function of the melting point of the solvent or wax preparation in the micro-capsules. It may be provided that the color change is adjusted to the temperature of the phase change of the thermoplastic resin or of the melting or recrystallization temperature and therefore correlates with the thermal and mechanical, particularly visco-elastic, material parameters (viscosity, shear modulus) of the thermoplastic resin. The phase change of the thermoplastic resin is characterized by a more or less pronounced hysteresis range $\Delta H_K$, which is to say the difference between the melting point and solidification point.

In general, heating the wax material and converting it into its liquid state results in a separation of two components that jointly produce the coloring effect in the micro-capsules, wherein the components only come in contact with one another again during the solidification of the wax material and then produce a visible color by means of electron interaction.

The hysteresis range $\Delta H_F$ of the micro-encapsulated thermochromic dyes is between 1 and approximately 10 K. Upon heating, the change in hue is completed at the upper temperature, and upon cooling it is completed accordingly at the lower temperature of the hysteresis range. In contrast, the thermoplastic resins generally have a broader hysteresis range $\Delta H_K$, which may comprise approximately 10 to 40 K. It is only due to this wide range of the phase change that it is possible to process the dressing materials within an acceptable time window.

According to the disclosure, it may be provided in a further embodiment that a further dye may be present. This further dye may be a non-micro encapsulated dye or particularly a further micro-encapsulated dye, with a further thermochromic dye being preferred. In particular, mixtures of micro-encapsulated dyes of different colors, with or without thermochromic properties, may be used in order to adjust a wide variety of color changes or color hues. A special embodiment, for example, may provide that the dressing material has a green color in the cold state and a yellow color in the activated state. In particular, it is also possible to use several types of micro-encapsulated thermochromic dyes with different color-turning temperatures. Depending on the current temperature, the gradual color may enable even better differentiation during heating or cooling. This visual signal effect allows both the user and the patient to precisely determine the solidification phase, and hence the remaining processing time, or it allows the patient to determine the present supporting effect and strength, and potentially prevent subsequent injury. In particular, also a signal effect can be achieved in that a first color change occurs when a certain processing state has been reached, wherein then a second temperature change signals that the preheated dressing material has reached a temperature state which would be considered uncomfortable by the patient.

Furthermore, by adding different thermochromic dyes, interesting visual effects can be achieved in that the color changes are adjusted such that upon a change of the ambient temperature also the dressing undergoes a color change, similar to the chameleon effect.

In particular, it may be provided that further textile webs and/or further thermoplastic resin layers are applied and the different layers are disposed to form a dressing. Possible thermoplastic resins, in principle, are such that are rigid or semi-rigid at temperatures of 40° C., particularly 50° C., or below. In particular also mixtures of different polymers may be used as the thermoplastic resin, provided that the polymers can be blended with one another. In particular, a hot-melt adhesive which melts at temperatures of 55° C. to 90° C., preferably of 60° C. to 80° C., particularly preferred of 60° C. to 70° C. and which remains pliable for some time, even after cooling to below the melting point, can be used as the polymer. To ensure that the thermoplastic resin can be used in a thermoplastic dressing material under normal application conditions, it must have a temperature resistance of up to 40° C., preferably up to 50° C., and particularly up to 55° C., and at these temperatures the polymer may not be subject to considerable softening or decomposition. It is preferable if the thermoplastic resin has a melt-flow index of 0.5 to 200 g/10 min. at 125° C., more preferred of 4 to 40 g/10 min., particularly preferred of 12-25 g/10 min., wherein the determination of the melt-flow index occurs according to DIN ISO 1133 at a test temperature of 125° C. and nominal load of 325 g. The hardening time after heating to or above the melting point depends on the temperature reached and the cooling speed and is generally 1 to 15 min., preferably 2 to 10 min., and preferred 3 to 8 min. Suitable thermoplastic resins with the above properties are, for example, polyester, polyurethane, polyvinyl acetate or also linear saturated polyester compounds. Such polyester is available commercially by the name of "CAPA Polycaprolactone" from Solvay Interox in Warrington, UK. In addition, the thermoplastic polymers may also comprise further adjuvants or additives, such as stabilizers, softeners, resins, tackifiers, UV filters, fillers, or antioxidants. Further thermoplastic polymers that may have a certain residual flexibility are, for example, polyethylene acrylic acid ester copolymers, ethyl-vinyl acetate copolymers and polyurethane. In this case, a body part to be provided with a dressing will not be completely fixed, but instead a certain level of mobility remains, enabling functional use of the affected body parts.

By providing a second textile web on the polymer layer, it is possible in particular that a resulting bandage is easy to unroll, even after heating and optional squeezing in a water bath. In addition, the application of an adhesive protective layer can be foregone, and the bandage can be directly rolled up. In addition, the wearing comfort increases as a result of the creation of a textile surface characteristic. Possible textile materials for the first or also for further textile webs are in principle elastic, but also non-elastic fibers and fiber materials. It is possible to use either synthetic or natural fibers. The textile webs used may be textile fibrous webs, but also nonwovens or wovens as well as fabrics or knitted textiles.

The thermochromic dyes can be, for example, the micro-encapsulated ChromaZone powders from TMC—Thermographic Measurements Ltd., Flintshire (UK).

The disclosure further relates to a bandage comprising the above-described dressing material. The bandage may be made in particular of the dressing material by unrolling. The disclosure further relates to the use of the above dressing material for the production of an orthopedic support dressing as well as a support dressing.

Finally, the disclosure also relates to a method for producing a dressing material comprising the following steps: Providing a textile web, mixing a thermoplastic polymer with at least a first micro-encapsulated dye and/or a color preparation comprising a first micro-encapsulated dye to produce a coating compound, coating the textile web with the coating compound, preferably applying a further textile web onto the coating compound, and customizing the dressing material, particularly by cutting it into web-like material of a defined length and width and/or winding it in rolls of a defined width and diameter. In this way, a bandage may be obtained. In particular, it may be provided that a cooling step is performed prior to the customizing step. So as to coat the textile web, furthermore heating may be required, and in particular an extrusion process is used.

The method furthermore comprises a step according to which the color preparation is produced by adding a micro-encapsulated dye to a carrier polymer, wherein the carrier polymer has a melting point $T_B$ in the range of 10 K below to 60 K above the melting point Tm of the polymer used to produce the thermoplastic dressing material.

In particular, the identical thermoplastic polymer may be used as the carrier polymer. The mixture of the carrier polymer and micro-encapsulated dye is melted, homogenized and granulated after cooling. Such a color preparation is generally referred to as a master batch. The master batch may comprise further additives, such as fillers, lubricants, stabilizers, and processing adjuvants.

Alternatively, it is possible to produce what is referred to as a liquid color, wherein the micro-encapsulated dyes are admixed to an inert fluid, particularly a mineral oil, ester oil, fatty acid ester, fatty alcohol or polyethylene glycol. In particular, monocarboxylic acid esters may be used as the liquid saturated fatty acid-fatty alcohol ester, for example n-hexyl laurate or n-octyl caprylate, as well as waxy saturated fatty acid-fatty alcohol esters, for example tallow alcohol palmitate stearate or pentaerythrite ester. It is also possible to provide adjuvants such as surfactants or stabilizers such as thixotropic agents, wherein a homogeneous dispersion is produced from the inert fluid and the micro-encapsulated dye present in powder form. The micro-encapsulated dye should be present in finely distributed form, free of pigment accumulations, in the fluid. Particular attention should be paid that the micro-capsules are not damaged, which would impair their color change function. The weight percentage of the micro-capsules with the dye may be adjusted to between 20 and 70%.

The invention will be explained in more detail hereinafter based on some examples. According to the disclosure, during the production of the thermoplastic dressing material, a heat-sensitive micro-encapsulated dye is added to a thermoplastic polymer with suitable melting and solidification points, so that the dye is distributed as homogeneously and finely dispersed in the polymer matrix as possible. The production of the thermoplastic dressing material is disclosed in DE 199 07 043 B4, which is hereby expressly included by reference.

Hereinafter, the production of the thermoplastic polymer will be explained, which is then used for coating purposes or impregnation or other bonding with the textile material. So as to achieve sufficiently fine distribution of the micro-capsules in the polymer matrix, and hence satisfactory color homogeneity, the micro-capsules are preferably not stirred directly into the molten polymer or added as powder to the extruder, but instead, in a prior step, are processed in a master batch (concentrated micro-capsule/polymer mixture with a portion of 20-50% of micro-capsules) or provided as a liquid color preparation (slurrying of the micro-capsules in suitable inert fluids with a portion of 30-70% of micro-capsules).

Example 1

Metered Addition from Master Batch

A master batch generally comprises a carrier polymer, the color pigment, and (optionally) additives such as fillers, lubricants, stabilizers, processing adjuvants. In the example, the same thermoplastic polymer that also serves the production of the thermoplastic dressing material is used as the carrier polymer for the production of the micro-capsule/dye master batch.

Then, 50 parts by weight of polycaprolactone from Solvay Interox, Warrington, UK (CAPA 640, melting point 57° C.) are placed in the form of white granules (pellets measuring 4 mm in size) at room temperature in a solid matter mixer and mixed homogeneously with 50 parts by weight of a micro-encapsulated blue dye (CHROMAZONE powder from TMC—Thermographic Measurements Ltd., Flintshire (UK), color color-turning temperature 47° C., hysteresis range 5.4 K). To improve homogenization, 1 to 2 g of a lubricant may be added in the form of waxes, oils, ester oils, as well as antistatic agents. The homogenized mixture is added via a funnel and feed mechanism into a single-screw or double-screw extruder and melted at 100° C. and is then further homogenized in the extruder by means of suitable agitation, mixing and conveying segments in the screw. Since the temperature of the molten material is above the color-turning temperature of the micro-encapsulated thermochromic dye, a colorless molten polymer material exits at the end of the extruder, the material being extruded by a round die (3 mm in diameter) into an endless strand, which is immediately routed through a cold water bath for cooling. The melt solidifies and forms a rigid strand with a deep blue color, which comes back due to the reversible hue change. The strand is fed directly to a pelletizer (chopper with rotating blades) and cut into cylindrical pellets measuring 4 mm in length and 3 mm in diameter. It is likewise possible to use other die geometries and pelletizing devices (belt granulation, head granulation) to produce square or lenticular pellets. Additionally, the melt exiting the extruder can be solidified in tubs to form blocks with edge lengths of, for example, 30×30×50 cm, and the blocks can then be cooled and ground into pellet fragments, thus achieving a particle size distribution of irregularly shaped pellets of 2 to 10 mm. According to the formulation, the master batch produced in this way comprises 50% parts by weight [sic] of the micro-capsule dye.

To produce the thermoplastic dressing material, again CAPA 640 is used in the form of white pellets as the thermoplastic polymer. To prepare the coloring process, a blend of 95% by weight of the white granules and 5% by weight of the above master batch is produced in a mixer and then homogenized. The master batch granules can also be continuously admixed to the white polymer pellets via a conventional gravimetric metering unit. This mixture is melted at 140° C. in a single-screw extruder on the coating system and discharged by a suitable slotted die as a colorless film, which is directly placed on the first textile web. Then, the second textile web is applied, and the resulting composite is routed through cooling rollers. The thermoplastic dressing material that is obtained changes its hue from colorless back to blue as it cools. The sheets are cut into 2.50 meter long strips measuring 10 cm in width and wound into bandages.

To apply them, the bandages are heated in a water bath at 70° C. for 7 minutes, wherein the hue of the polymer coating changes from blue to transparent and the bandage overall appears to be white (basic color of the textile). This color change indicates the complete thermal activation of the bandage, which is now moldable and therefore ready for its actual use, the application on the body part. In this state, the material additionally at least adheres to itself. When wound onto the body part, the individual layers stick together to form a layer composite. The dressing slowly cools down within a period of 10 minutes and then solidifies again, wherein the blue hue continuously reappears as the color-turning temperature of the micro-encapsulated thermochromic dye is no longer met, thus visually indicating the strengthening of the dressing and the developing supporting effect/stabilization of the body part to be treated. After cooling off completely to room temperature, the finished support dressing has the original blue hue of the initial bandage. The color change from blue to white back to blue occurs reversibly every time when the cold support dressing is worked thermally (hair dryer, hot air gun), for example to smoothen the edges or change the shape of the dressing, and in doing so the color-turning temperature of the micro-encapsulated thermochromic dye is first exceeded and during cooling is again no longer met. This provides the user with a visual signal based on the respective hue, which indicates the activation state of the thermoplastic dressing material and hence the moldability/plasticity or rigidity. Similarly, based on the color change the patient is given a visual signal when the dressing, for example under the effect of too much heat (sun bathing, sauna), is softening and there is a risk that the supporting effect is lost.

Example 2

Metered Addition from Liquid Color

To produce the liquid color, the micro-encapsulated dye, present as a pigment powder, is converted into a homogeneous solution in an inert fluid, for example mineral oil, ester oil, fatty acid ester, fatty alcohols, polyethylene glycols etc., with the help of a dispersing agent while adding adjuvants, such as surfactants, or stabilizers, or thixotropic agents, so that the micro-encapsulated thermochromic dye is provided in the fluid in finely distributed form, which is to say free of pigment accumulations. The agitation speed and shear conditions must be adjusted such that the casing of the micro-capsules is not damaged and the capsule as such remains intact. The weight percentage of the micro-capsules with the dye in the liquid color is expediently adjusted to between 20 and 70% by weight. Liquid colors of this type, comprising micro-encapsulated thermochromic dyes, however, tend toward sedimentation and require stirring prior to use to ensure sufficient homogeneity.

In the manner just described, the following liquid color preparations F1 and F2 were prepared:

F1: 30 parts by weight of a micro-encapsulated blue dye (CHROMAZONE pigment from TMC—Thermographic Measurements Ltd., Flintshire (UK), color-turning temperature 47° C., hysteresis range 5.4 K) are dispersed in 70 parts by weight of n-octyl caprylate, resulting in a 30% liquid color of the micro-encapsulated thermochromic dye (hue: deep blue).

F2: 50 parts by weight of a micro-encapsulated red dye (CHROMAZONE pigment from TMC—Thermographic Measurements Ltd., Flintshire (UK), color-turning temperature 31° C., hysteresis range 7.5 K) are dispersed in 50 parts by weight of n-octyl caprylate, resulting in a 50% liquid color of the micro-encapsulated thermochromic dye (hue: deep red).

The two preparations F1 and F2 are filled into separate pressurized reservoirs and pumped through separate pressure hoses by applying excess air pressure, wherein a needle valve is provided at the end of each hose, which is opened and closed via the control solenoid. Due to the excess pressure, an even flow of liquid color is discharged when the valve is open.

To coat the textile carrier, a device equivalent to the device used in Example 1 is used. The coloring process of the white CAPA 640 thermoplastic polymer is performed as follows: The two needle valves, connected to the pressurized supply reservoirs of the liquid color, are installed directly next to each other in the extruder head, which is used to melt the white polymer. The needle valves can be controlled separately by means of an electronic control unit, so that via the needle valve opening and closing cycle times a defined liquid color flow is discharged into the flow of the white polymer melt, which is to say a metered addition of the respective liquid color into the polymer flow is possible.

In the present example the controller is adjusted such that on average over time 1 g of liquid color F1 and 1 g of liquid color F2 are metered into 98 g of polymer material. Under the effects of the rotating extruder die, the liquid colors are homogeneously distributed in the 140° C. hot polymer melt. Since the color-turning temperature of the micro-encapsulated thermochromic dye is being exceeded, the melt discharged from the slotted die at the end of the extruder is again transparent.

In the cooled state (at room temperature 22° C.), the thermoplastic dressing material produced equivalent to Example 1 has a purple hue, which is obtained as a subtractive color from red and blue.

To apply the bandages that are produced from the coated textile web, they are heated in a water bath at 70° C. for 7 minutes, wherein the hue of the polymer coating changes from purple briefly to blue and then to transparent and the bandage overall appears to be white (basic color of the textile). This color change indicates the complete thermal activation of the bandage, which is now moldable and therefore ready for its actual use, the application on the body part. When wrapped onto the body part, the layers stick together, and with this layer composite the dressing slowly cools off and solidifies again, wherein at first the blue hue continuously reappears as the color-turning temperature of the micro-encapsulated thermochromic dye F1 at 47° C. is no longer met and the developing supporting effect/stabilization of the body part to be treated is indicated. Upon further cooling toward room temperature, the red base color of the micro-encapsulated thermochromic dye F2 returns at 31° C., which causes the previously blue hue to change to the purple mixed hue. After cooling off completely, the finished support dressing at room temperature, 22° C., has again the original purple hue of the initial bandage.

The change of color from purple to blue to white to blue and back to purple occurs reversibly each time during the heating/cooling cycles and indicates the respective temperature that the support dressing has at that time (within the hysteresis range of the respective color-turning temperatures of the micro-encapsulated thermochromic dyes). The multiple color changes enable an even more precise assessment of the respective state of the thermoplastic dressing. The blue hue signals the onsetting solidification of the previously applied bandage, and the color change to purple occurring during further cooling indicates the state when the maximum final strength/stability of the dressing has been reached. During thermal processing by means of a hair dryer etc., the multiple color changes thus provide the user, based on the respective hue, with detailed information about the temperature and the rigidity of the thermoplastic dressing material and hence a graduated indication of the moldability/plasticity or stability level. Similarly, based on the multiple color changes the patient is given a visual indication, possibly serving as a warning and intervention limit, when the dressing, for example under the effect of too much heat (sun bathing, sauna), is softening and there is a risk that the supporting effect is lost.

The graphical illustration according to FIG. 1 explains the correlations of Example 2 and the invention again in more detail. To characterize the visco-elastic properties of the thermoplastic polymer across the entire temperature range of the phase change, the dynamic-mechanical analysis is used, wherein the polymer is placed between two plane-parallel plates which are caused to vibrate by means of a rotary vibration system (piezo rotary vibrator). By measuring the shear stress and the associated forces, the complex shear modulus G* is determined, which is comprised of the storage modulus G' (elastic portion) and the loss modulus G'' (viscous portion), which are connected to one another via the loss angle tan δ (phase shift). FIG. 1 shows the temperature-dependent course of the storage modulus G' (elastic portion of the shear modulus) determined in this way in the temperature range from 20° C. to 80° C. At room temperature (25° C.), the polymer assumes a solid state and G' has values in the range of $10^7$ Pascal (Pa). Upon heating, the shear modulus follows the curve L, wherein the phase transformation from solid to liquid at the melting temperature Tm is characterized by a clear drop in the shear modulus to approximately $10^4$ Pa, which then only decreases further minimally down to the temperature of 80° C. for the polymer melt. During the subsequent cooling of the melt, the shear modulus follows the curve S, wherein at the solidification temperature Tr again a clear increase in the shear modules from $10^5$ to $10^7$ Pa can be observed. The variance of the heating curve L and cooling curve S designates the hysteresis effect, wherein the hysteresis range of the thermoplastic polymer is derived from the difference $\Delta H_K = Tm - Tr$.

In FIG. 1, furthermore the micro-encapsulated thermochromic dyes F1 (blue hue) and F2 (red hue) from Example 2 are shown, along with the respective color-turning temperatures $T_{u1}$ and $T_{u2}$ as well as the associated hysteresis ranges $\Delta H_{F1}$ and $\Delta H_{F2}$. The color saturation of the thermochromic dye is at its maximum at the lower temperature limit of the hysteresis range and at its minimum at the upper temperature limit (transparent state). Based on the graph, the effect according to the invention can be seen, according to which upon heating of the thermoplastic polymer dyed with F1 and F2 (curve L) the purple base hue, starting at approximately 35° C., begins to turn as a result of the occurring color change of the dye F2 into the blue hue (base hue of F1) at around 35° C., which then becomes transparent upon further heating at about 50° C. only by the color change of the dye F1. During the melting process, the transparency is also maintained for the liquid polymer at temperatures up to 80° C. Upon cooling (curve S), the color change from transparent to blue begins in the still molten state of the thermoplastic polymer as it reaches the hysteresis range $\Delta H_{F1}$ of F1, which is approximately in the middle of the hysteresis range $\Delta H_K$ of the thermoplastic polymer. This first color change signals the onsetting solidification of the thermoplastic polymer, which then after complete solidification, which is to say in the rigid state, has a blue hue in this temperature range as well. Upon further cooling and as the hysteresis range $\Delta H_{F2}$ of F2 is reached, which is below the solidification temperature Tr, the color change from blue to purple occurs (triggered by the color change of F2 from transparent to red). This second color change signals the complete recrystallization during solidification of the thermoplastic polymer, and hence, in the finished thermoplastic dressing material, the maximum supporting effect during the functional phase when the dressing is worn.

An essential characteristic of the invention is that the dyes F1, F2—with respect to the position of the color-turning temperatures Tu and the hysteresis range, can be placed arbitrarily anywhere on the temperature scale, and therefore they can be adjusted to the hysteresis properties of the thermoplastic polymer and the intended signaling effect of the color change or the correlation with the visco-elastic properties.

In the manner described above, it is particularly easy to prevent danger to the patient from toxic dyes, and in particular when using thermochromic dyes, the change in the dressing's state, but also further processing and material parameters, can be signaled to the user and/or patient.

Further areas of applicability will become apparent from the description provided herein. It should be understood that the description and specific examples are intended for purposes of illustration only and are not intended to limit the scope of the present disclosure.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A dressing material, comprising a thermoplastic polymer, the thermoplastic polymer being applied to a first textile web, wherein the thermoplastic polymer has a hysteresis range between approximately 10 K and approximately 40K and comprises a first micro-encapsulated dye having a hysteresis range between approximately 1 K and approximately 10 K, wherein a change in hue is completed at an upper temperature and a lower temperature of the hysteresis ranges upon heating and cooling, respectively, and the thermoplastic polymer has a storage modulus G' between approximately $10^4$ Pa and $10^7$ Pa.

2. The dressing material according to claim 1, wherein the first micro-encapsulated dye is a thermochromic dye.

3. The dressing material according to claim 1, wherein the thermoplastic polymer comprises at least a second dye.

4. The dressing material according to claim 3, wherein at least the second dye is a micro-encapsulated and particularly a thermochromic dye.

5. The dressing material according to claim 1, wherein at least the first and/or the further thermochromic dyes with respect to their color-turning points Tu correlate with the thermal and/or mechanical material and/or processing parameters of the thermoplastic polymer.

6. The dressing material according to claim 1, wherein further textile webs and/or thermoplastic polymer layers are provided and may form a composite.

7. The dressing material according to claim 1, wherein the dressing is an orthopedic support dressing.

8. The dressing material according to claim 1, wherein the dressing is a bandage for producing an orthopedic support dressing.

* * * * *